United States Patent
Miyoshi et al.

(10) Patent No.: US 11,453,904 B2
(45) Date of Patent: Sep. 27, 2022

(54) EVALUATION METHOD FOR PERMEABILITY OF POROUS MEMBRANE, CELL EVALUATION METHOD, AND DRUG EVALUATION METHOD

(71) Applicant: FUJIFILM CORPORATION, Tokyo (JP)

(72) Inventors: Hayato Miyoshi, Kanagawa (JP); Takahiro Oba, Kanagawa (JP); Keisuke Oku, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 0 days.

(21) Appl. No.: 17/693,433

(22) Filed: Mar. 14, 2022

(65) Prior Publication Data

US 2022/0195488 A1 Jun. 23, 2022

Related U.S. Application Data

(63) Continuation of application No. PCT/JP2020/018941, filed on May 12, 2020.

(30) Foreign Application Priority Data

Sep. 18, 2019 (JP) .............................. JP2019-169806

(51) Int. Cl.
 *C12Q 1/18* (2006.01)
 *G01N 15/08* (2006.01)
(52) U.S. Cl.
 CPC .............. *C12Q 1/18* (2013.01); *G01N 15/08* (2013.01); *G01N 2015/086* (2013.01); *G01N 2015/0846* (2013.01)

(58) Field of Classification Search
 CPC . C12Q 1/00; C12Q 1/18; G01N 15/00; G01N 15/08; G01N 2015/0846; G01N 2015/086
 See application file for complete search history.

(56) References Cited

U.S. PATENT DOCUMENTS 8,117,899 B2 * 2/2012 Piombini ........... G01N 15/0826
                                                       73/38
2007/0248985 A1 10/2007 Dutta et al.
(Continued)

FOREIGN PATENT DOCUMENTS

JP      S61-175547 A    8/1986
JP      H01-134244 U    9/1989
(Continued)

OTHER PUBLICATIONS

International Search Report issued in International Application No. PCT/JP2020/018941 dated Jul. 21, 2020.
(Continued)

*Primary Examiner* — Nguyen Q. Ha
(74) *Attorney, Agent, or Firm* — Solaris Intellectual Property Group, PLLC

(57) ABSTRACT

There is provided an evaluation method for permeability of a porous membrane that separates a first flow channel and a second flow channel, the evaluation method including supplying a pressure to a liquid inside the first flow channel and acquiring a change that occurs in a liquid accommodated in the second flow channel as an evaluation indicator of permeability of the porous membrane.

6 Claims, 12 Drawing Sheets

(56) References Cited

U.S. PATENT DOCUMENTS

2012/0324984 A1   12/2012  Wakefield et al.
2020/0385664 A1*  12/2020  Oba ...................... C12M 35/00
2021/0041339 A1*   2/2021  Tsilomelekis ...... G01N 33/0057

FOREIGN PATENT DOCUMENTS

| JP | H08-101212 A |   | 4/1996 |   |
|----|---|---|---|---|
| JP | 2010-207143 A |   | 9/2010 |   |
| JP | 2010207143 A | * | 9/2010 | .............. C12M 1/34 |
| JP | 2013-512448 A |   | 4/2013 |   |
| JP | 2013-167645 A |   | 8/2013 |   |
| JP | 2016-090381 A |   | 5/2016 |   |

OTHER PUBLICATIONS

Written Opinion of the ISA issued in International Application No. PCT/JP2020/018941 dated Jul. 21, 2020.

* cited by examiner

FIG. 13

START

→ THE UPPER MICRO FLOW CHANNEL IS FILLED WITH A LIQUID CONTAINING A PHOSPHOR —S11

→ THE LOWER MICRO FLOW CHANNEL IS FILLED WITH A LIQUID CONTAINING NO PHOSPHOR —S12

→ THE LIQUID THAT CONTAINS A PHOSPHOR IS SUPPLIED TO THE UPPER MICRO FLOW CHANNEL WHILE THE SUPPLY PRESSURE IS BEING CHANGED —S13

→ THE CHRONOLOGICAL CHANGE OF THE FLUORESCENT LIGHT AMOUNT IS ACQUIRED —S14

END

FIG. 14

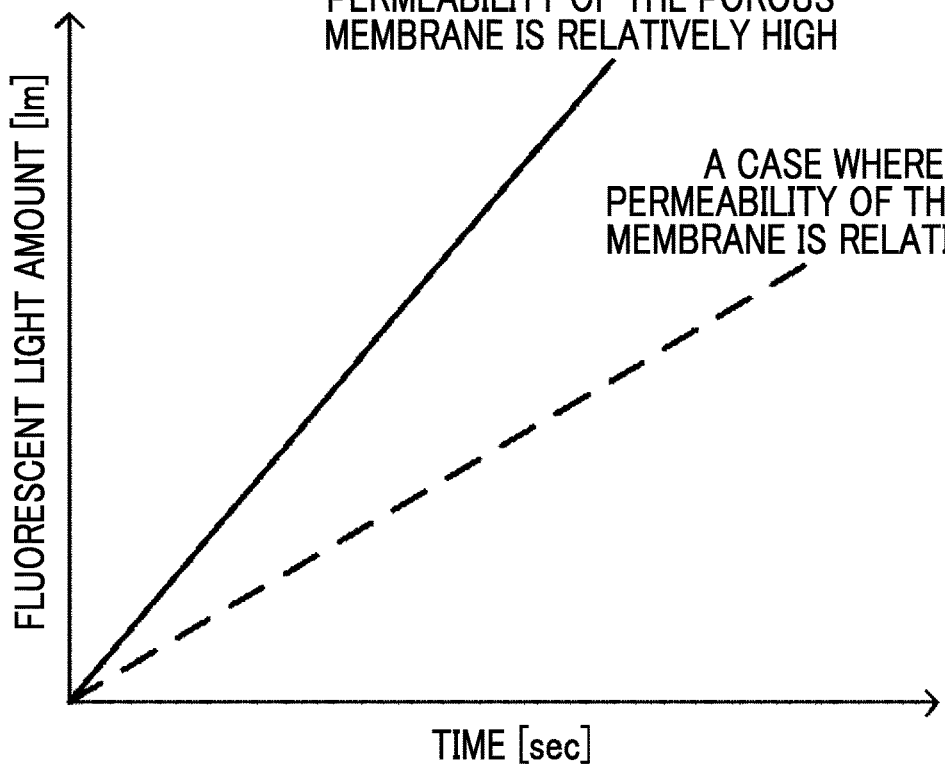

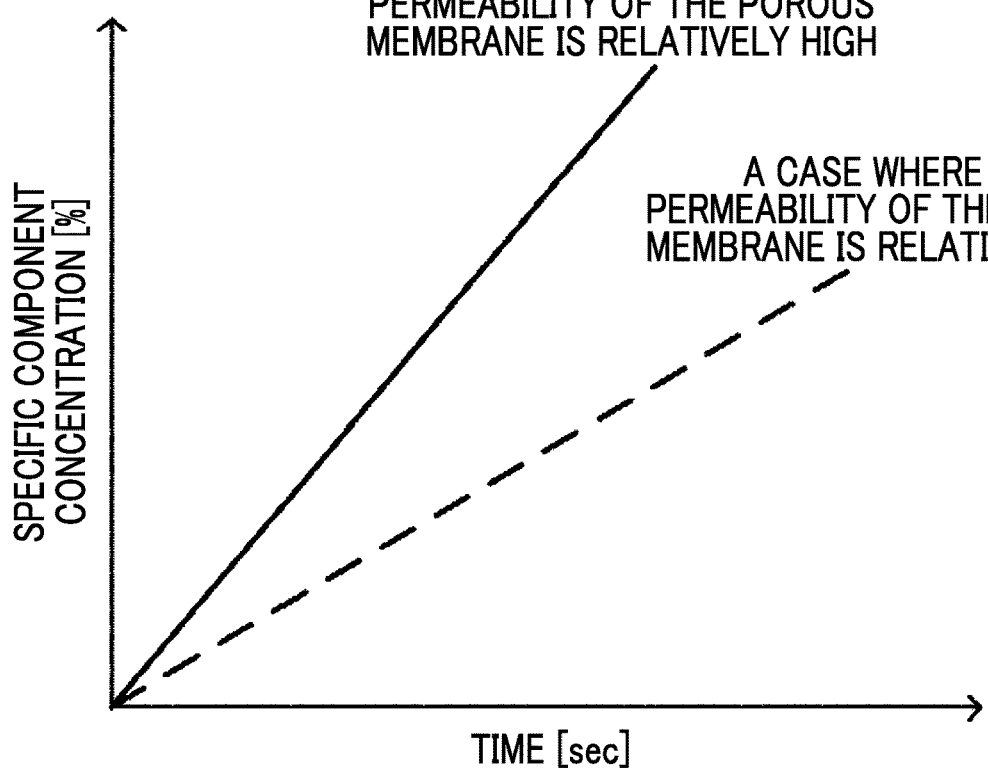

EVALUATION METHOD FOR PERMEABILITY OF POROUS MEMBRANE, CELL EVALUATION METHOD, AND DRUG EVALUATION METHOD

CROSS-REFERENCE TO RELATED APPLICATIONS

This application is a continuation application of International Application No. PCT/JP2020/018941, filed May 12, 2020, the disclosure of which is incorporated herein by reference in its entirety. Further, this application claims priority from Japanese Patent Application No. 2019-169806, filed on Sep. 18, 2019, the disclosure of which is incorporated herein by reference in its entirety.

BACKGROUND

1. Technical Field

The present disclosed technology relates to an evaluation method for permeability of a porous membrane, a cell evaluation method, and a drug evaluation method.

2. Description of the Related Art

The following techniques are known as a method for observing cells using a microfluidic device. For example, JP2010-207143A discloses a device for cell observation, which includes a cell culture chamber and a chemical liquid chamber adjacent to each other through a porous membrane, an introduction channel and a discharge channel for discharging a cell-containing solution after introduction into a cell culture chamber, an introduction channel and a discharge channel for discharging a chemical liquid after introduction into the chemical liquid chamber, and an observation window provided on a side of the chemical liquid chamber opposite to the porous membrane. Further, JP2010-207143A discloses a cell observation method in which a cell-containing solution is introduced into a cell culture chamber and a chemical liquid is introduced into a chemical liquid chamber, and luminescence light based on cells or a product from the cells is observed through an observation window.

In addition, JP1996-101212A (JP-H8-101212A) describes that in a filtration cell having a sample liquid passage and a carrier liquid passage, which are in contact with each other through a porous membrane, a carrier obtained by moving at least a part of a sample in a liquid to be measured into a carrier through the porous membrane is injected into a detector by an injector.

SUMMARY

In a microfluidic device having a first flow channel, a second flow channel, and a porous membrane that separates these flow channels, the following method can be considered as an evaluation method for permeability of a porous membrane. For example, a method of monitoring an amount of light radiated from a phosphor that leaks into the second flow channel can be considered, where a liquid containing a phosphor is accommodated in a first flow channel, a liquid containing no phosphor is accommodated in a second flow channel, and the phosphor diffuses in a liquid and permeates through a porous membrane to leak to the second flow channel. However, according to this method, since the diffusion rate of the phosphor is low, it takes a lot of time (for example, about 60 minutes) to carry out an evaluation.

The present disclosed technology has been made in consideration of the above point, and one aspect of the technique is to evaluate the permeability of a porous membrane in a short time.

An evaluation method according to the present disclosed technology is an evaluation method for permeability of a porous membrane that separates a first flow channel and a second flow channel, the evaluation method comprising supplying a pressure to a liquid inside the first flow channel and acquiring a change that occurs in a liquid accommodated in the second flow channel as an evaluation indicator of permeability of the porous membrane.

An evaluation method according to the present disclosed technology is an evaluation method for permeability of a porous membrane that is inserted between a first flow channel and a second flow channel, the evaluation method comprising acquiring a change that occurs inside a liquid accommodated in the second flow channel as an evaluation indicator of permeability of the porous membrane in a case of supplying a liquid to the first flow channel while changing a supply pressure.

According to the evaluation method according to the embodiment of the present disclosed technology, it is possible to evaluate the permeability of the porous membrane in a short time.

A chronological change of a flow rate of the liquid that passes through the second flow channel may be acquired as the evaluation indicator. In addition, a phosphor is contained in the liquid that is supplied to the first flow channel, and a chronological change in an amount of light radiated from the phosphor contained in the liquid that flows through the second flow channel may be acquired as the evaluation indicator. Further, a specific component is contained in the liquid that is supplied to the first flow channel, and a chronological change in a concentration of the specific component contained in the liquid that flows through the second flow channel may be acquired as the evaluation indicator.

The cell evaluation method according to the present disclosed technology is a cell evaluation method using the above-described evaluation method for permeability of a porous membrane, the cell evaluation method comprising acquiring the evaluation indicator acquired in a state where cells to be evaluated are cultured on a surface of the porous membrane as an indicator of performance of the cells to be evaluated, the performance being blocking of leakage of a liquid that is supplied to the first flow channel to the second flow channel.

The drug evaluation method according to the present disclosed technology is a drug evaluation method using the above-described evaluation method for permeability of a porous membrane, the cell evaluation method comprising culturing cells on a surface of the porous membrane and acquiring the evaluation indicator acquired after exposing the cells to a drug to be evaluated as an indicator of toxicity of the drug to be evaluated to the cells.

In the evaluation method according to the present disclosed technology, a microfluidic device having the first flow channel and the second flow channel may be used.

According to the present disclosed technology, it is possible to evaluate the permeability of the porous membrane in a short time.

BRIEF DESCRIPTION OF THE DRAWINGS

Exemplary embodiments according to the technique of the present disclosure will be described in detail based on the following figures, wherein:

FIG. 13 is a flowchart illustrating an example of an evaluation method for permeability of a porous membrane according to another embodiment of the present disclosed technology;

FIG. 14 is a graph illustrating an example of a time course of a fluorescent light amount in a case where the supply pressure is linearly changed in time;

FIG. 17 is a flowchart illustrating an example of an evaluation method for permeability of a porous membrane according to another embodiment of the present disclosed technology;

FIG. 18 is a graph illustrating an example of a time course of a specific component concentration in a case where the supply pressure is linearly changed in time;

DETAILED DESCRIPTION

Figure 1:
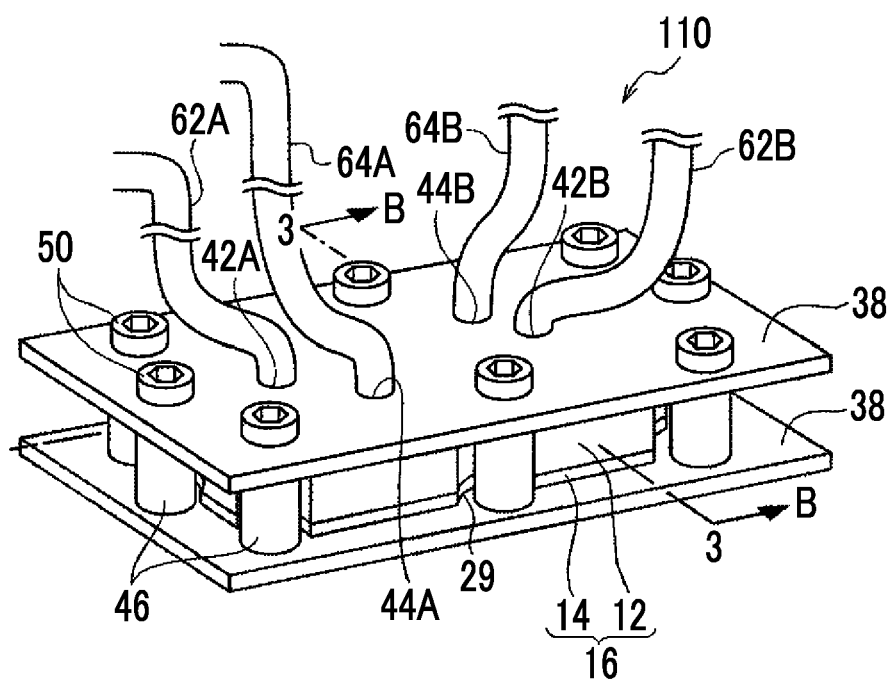
FIG. 1 is a perspective view illustrating an example of a configuration of a microfluidic device according to an embodiment of the present disclosed technology.

Hereinafter, embodiments of the present invention will be described with reference to the drawings. In each of the drawings, substantially the same or equivalent configuration elements or parts are designated by the same reference numeral.

Figure 2:
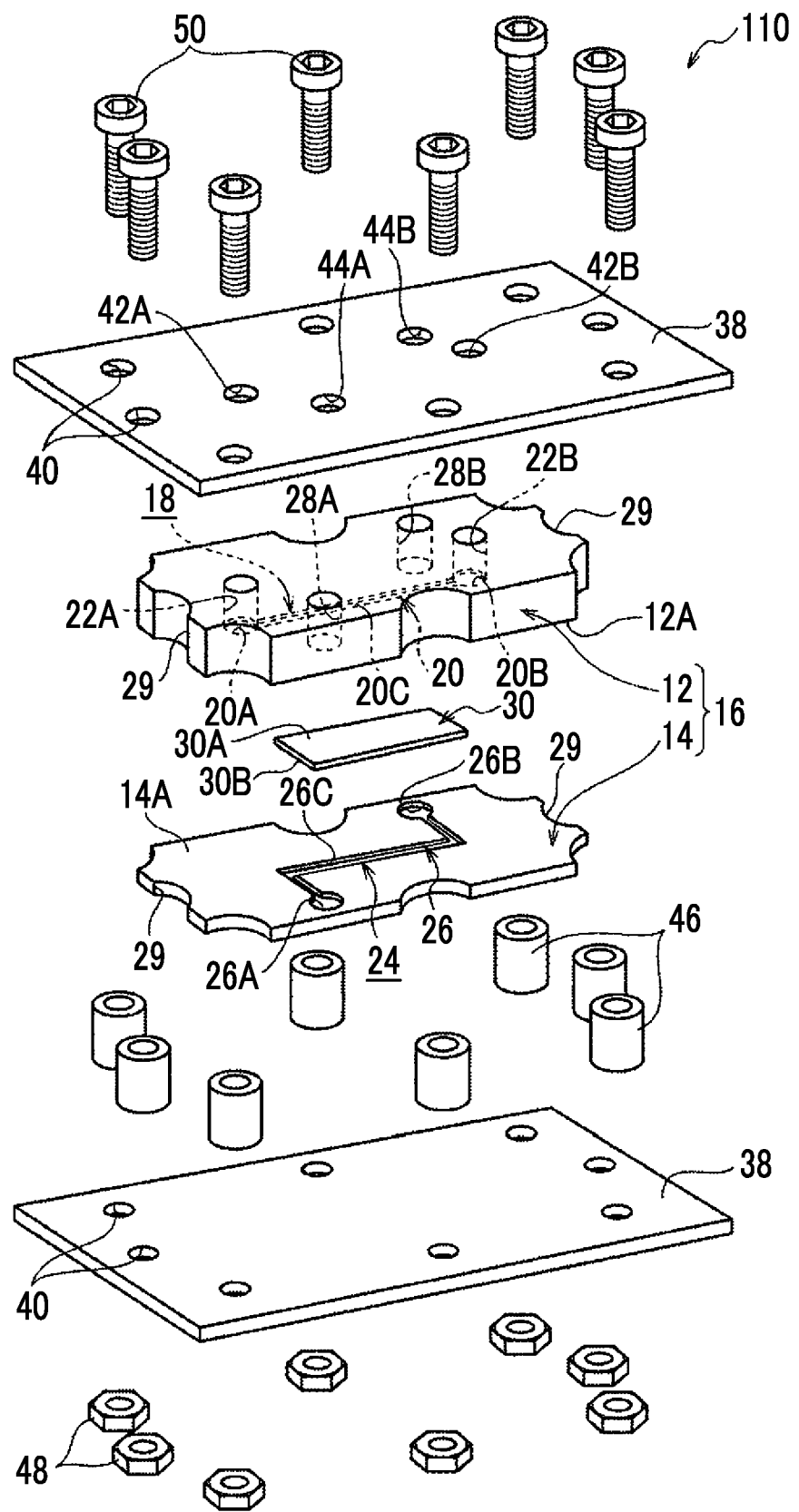
FIG. 2 is an exploded perspective view of a microfluidic device according to the embodiment of the present disclosed technology.
Figure 3:
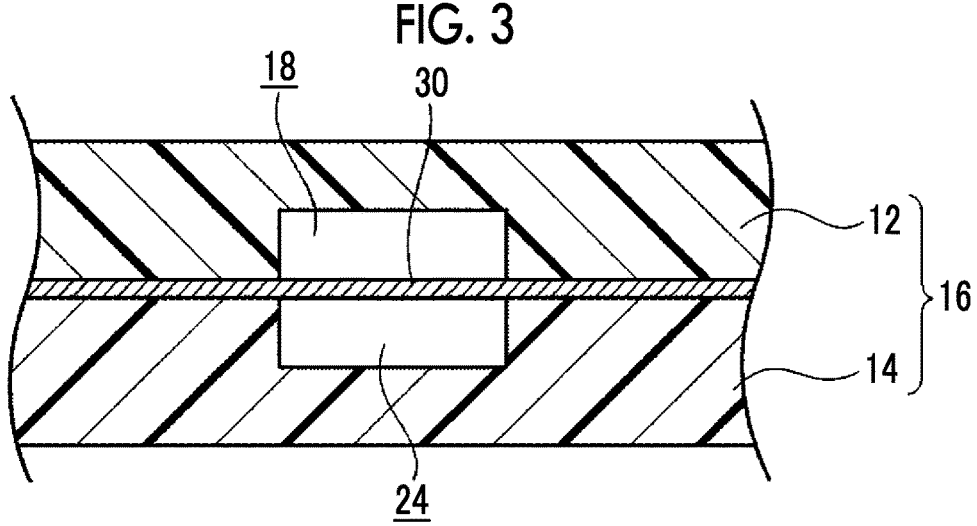
FIG. 3 is a schematic view illustrating a part of a cross section taken along a line 3-3 in FIG. 1.

FIG. 1 is a perspective view illustrating an example of a configuration of a microfluidic device 110 according to an embodiment of the present disclosed technology, where the microfluidic device 110 is used for the evaluation of the permeability of the porous membrane, and FIG. 2 is an exploded perspective view of the microfluidic device 110. FIG. 3 is a schematic view illustrating a part of a cross section taken along a line 3-3 in FIG. 1. The microfluidic device 110 has a cavity unit 16 composed of an upper cavity member 12 and a lower cavity member 14, which are opposite to each other, as a pair of cavity members laminated in the thickness direction. The upper cavity member 12 and the lower cavity member 14 are made of a material having flexibility, such as polydimethylsiloxane (PDMS) as an example. It is noted that as the material that constitutes the upper cavity member 12 and the lower cavity member 14, in addition to PDMS, an epoxy resin, a urethane resin, a styrenic thermoplastic elastomer, an olefinic thermoplastic elastomer, an acrylic thermoplastic elastomer, or a polyvinyl alcohol, can be used.

As illustrated in FIG. 2, a recessed part 26 that defines a lower micro flow channel 24 is formed on the upper surface of the lower cavity member 14, that is, on an opposite surface 14A opposite to the upper cavity member 12. The lower micro flow channel 24 is an example of a second flow channel in the present disclosed technology. The recessed part 26 has an inflow port 26A, an outflow port 26B, and a flow channel part 26C that makes the inflow port 26A and the outflow port 26B communicate with each other.

Similarly, a recessed part 20 that defines an upper micro flow channel 18 is formed on the lower surface of the upper cavity member 12, that is, on an opposite surface 12A opposite to the lower cavity member 14. The upper micro flow channel 18 is an example of a first flow channel in the present disclosed technology. The recessed part 20 has an inflow port 20A, an outflow port 20B, and a flow channel part 20C that makes the inflow port 20A and the outflow port 20B communicate with each other. In addition, through-holes 22A and 22B that penetrate the upper cavity member 12 in the thickness direction are provided in the upper cavity member 12. The lower ends of the through-holes 22A and 22B respectively communicate with the inflow port 20A and the outflow port 20B.

The inflow port 26A and the outflow port 26B of the lower cavity member 14 are provided at positions where they do not overlap with the inflow port 20A and the outflow port 20B of the upper cavity member 12 in a case of being viewed in a plan view. On the other hand, the flow channel part 26C of the lower cavity member 14 is provided at a position where it overlaps with the flow channel part 20C of the upper cavity member 12 in a case of being viewed in a plan view.

Through-holes 28A and 28B, which penetrate the upper cavity member 12 in the thickness direction and of which lower ends respectively communicate with the inflow port 26A and the outflow port 26B of the lower cavity member 14, are provided in the upper cavity member 12. On the outer peripheral surface of the cavity unit 16, recessed parts 29 are provided at positions where spacers 46 are arranged.

A porous membrane 30 is arranged between the opposite surfaces 12A and 14A of the upper cavity member 12 and lower cavity member 14. An upper surface 30A and a lower surface 30B of the porous membrane 30 cover the flow channel parts 20C and 26C of the upper micro flow channel 18 and lower micro flow channel 24, and they separate the upper micro flow channel 18 and the lower micro flow channel 24. That is, the lower micro flow channel 24 and the upper micro flow channel 18 are adjacent to each other with the porous membrane 30 being interposed therebetween. Specifically, the upper surface 30A of the porous membrane 30 defines the upper micro flow channel 18 together with the recessed part 20 of the upper cavity member 12, and the lower surface 30B of the porous membrane 30 defines the lower micro flow channel 24 together with the recessed part 26 of the lower cavity member 14.

The porous membrane 30 is constituted to include, for example, a hydrophobic polymer that can be dissolved in a hydrophobic organic solvent. It is noted that the hydrophobic organic solvent is liquid of which the solubility in water at 25° C. is 10 (g/100 g water) or less. Examples of the hydrophobic polymer include polystyrene, polyacrylate, and polymethacrylate.

Figure 4A:
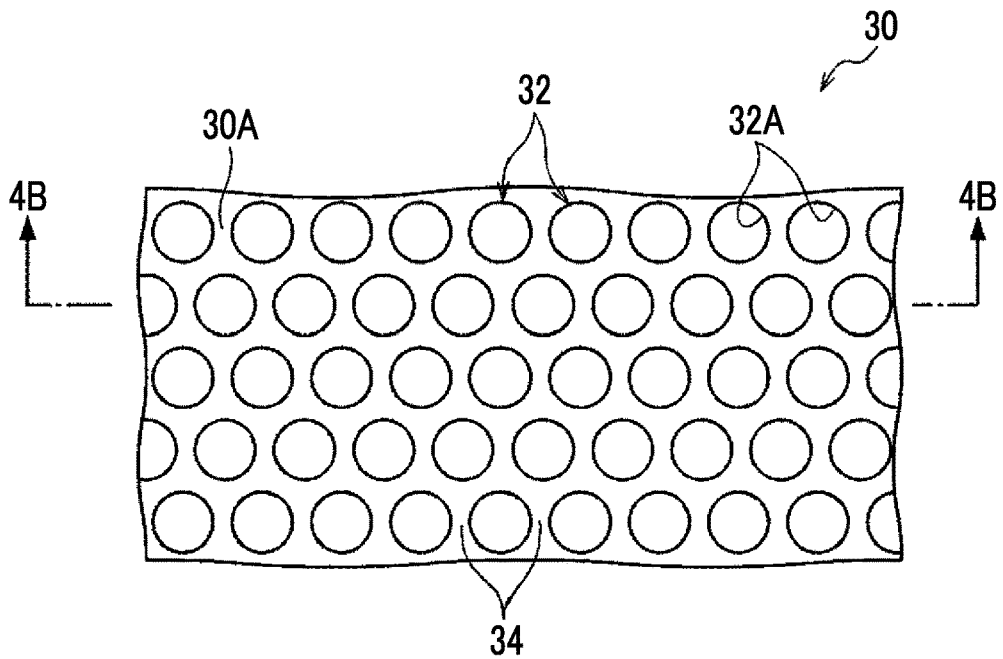
FIG. 4A is a plan view illustrating an example of a configuration of a porous membrane according to an embodiment of the present disclosed technology.
Figure 4B:
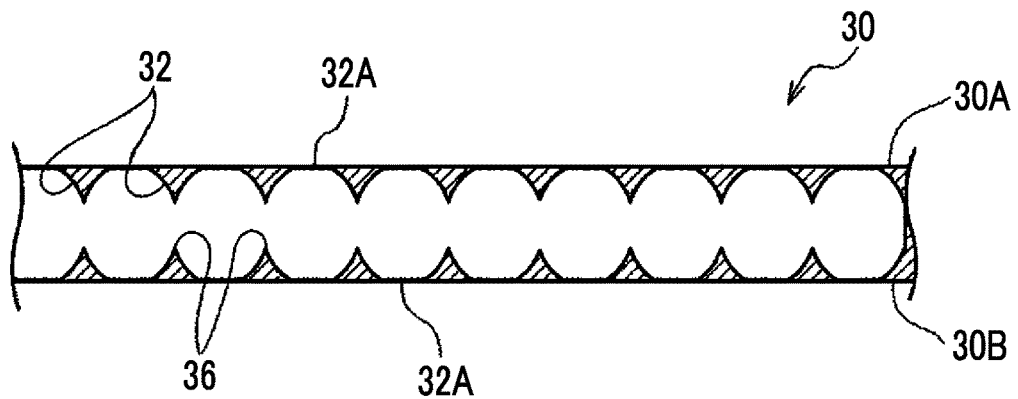
FIG. 4B is a cross-sectional view taken along a line 4B-4B in FIG. 4A.

FIG. 4A is a plan view illustrating an example of the configuration of the porous membrane 30. FIG. 4B is a cross-sectional view taken along a line 4B-4B in FIG. 4A. A plurality of intramembrane spaces 32 that penetrate the porous membrane 30 in the thickness direction are formed in the porous membrane 30, and openings 32A of the intramembrane space 32 are provided on both surfaces of the upper surface 30A and the lower surface 30B of the porous membrane 30. In addition, the opening 32A has a circular shape in a case of being viewed in a plan view. The openings 32A are provided to be spaced from each other, and a flat portion 34 extends between the openings 32A adjacent to each other. The shape of the opening 32A is not limited to a circular shape, and it may be a polygonal shape or an elliptical shape.

As illustrated in FIG. 4A, the plurality of openings 32A are arranged in a honeycomb shape. Here, the honeycomb-shaped arrangement refers to an arrangement in which six openings 32A are equally arranged around any opening 32A (excluding the opening 32A at the edge of the membrane), centers of the six openings 32A are located at the apexes of a regular hexagon, and the center of the opening 32A located at the centers of the six openings 32A corresponds to the center of the regular hexagon. The description "equally arranged" referred to herein does not necessarily mean that the openings 32A are arranged accurately at a central angle of 60°, and it suffices that the surrounding six openings 32A are arranged at substantially equal spacings with respect to the opening 32A located at the center. It is noted that "the center(s) of the opening(s) 32A" means the center(s) of the opening(s) 32A in a case of being viewed in a plan view.

As illustrated in FIG. 4B, the intramembrane space 32 of the porous membrane 30 has a shape of spherical segment obtained by cutting an upper end and a lower end of a sphere. The sphere referred to herein does not have to be a true sphere, and it has a degree of distortion that is generally allowed to be recognized as a sphere. In addition, the intramembrane spaces 32 adjacent to each other have a lateral communication structure in which communication holes 36 communicate with each other in the inside of the porous membrane 30. It is noted that the lateral communication structure refers to a space structure in which the adjacent intramembrane spaces 32 communicate with each other in the inside of the porous membrane 30. The description "lateral" referred to herein means a plane direction orthogonal to the vertical direction in a case where the thickness direction of the porous membrane 30 is vertical. In the porous membrane 30, since the openings 32A are arranged in a honeycomb shape, any intramembrane space 32 communicates with all of the six intramembrane spaces 32 that are equally arranged around the porous membrane 30. It is noted that the intramembrane space 32 may have a barrel shape, a circular columnar shape, a polygonal columnar shape, or the like, and the communication hole 36 may be a tubular void that connects the adjacent intramembrane spaces 32 to each other.

The average opening diameter of the opening 32A is preferably 1 µm or more and 200 µm or less. In a case where the average opening diameter of the openings 32A is set to 1 µm or more, it is easy to form the lateral communication structure of the intramembrane space 32. In addition, in a case where the average opening diameter of the openings 32A is set to 200 µm or less, it is easy to maintain a honeycomb-shaped arrangement without the adjacent openings 32A being fused with each other. It is noted that the average opening diameter means the average value of the diameters of the plurality of openings 32A on the surface of the porous membrane 30. The average opening diameter can be, for example, an average value obtained by observing the surface of the porous membrane 30 under a microscope and measuring the diameters of a considerable number of openings 32A.

The void ratio of the porous membrane 30 is preferably 40% or more and 90% or less. In a case where the void ratio of the porous membrane 30 is set to 40% or more, it is easy to form the lateral communication structure of the intramembrane space 32. In a case where the void ratio of the porous membrane is set to 30% to 90% or less, it becomes easy to maintain the shape of the porous membrane 30, and thus the strength does not decrease and the porous membrane 30 becomes difficult to be torn. It is noted that the void ratio refers to the ratio of the volume of the intramembrane space 32 with respect to the volume of the porous membrane 30. This void ratio can be determined as a percentage which is obtained by, for example, observing the cross section of the porous membrane 30 under a microscope, and dividing the volume of the plurality of intramembrane spaces 32 by the volume of the porous membrane 30 in which the intramembrane spaces 32 are present, where the volume thereof has been determined by estimating that the observed intramembrane spaces 32 have a shape of spherical segment obtained by cutting two upper and lower sides and six lateral sides of a sphere.

The membrane thickness of the porous membrane 30 is preferably 0.5 µm or more and 100 µm or less. Here, the numerical value of this membrane thickness is a numerical value derived from the fact that practically, the aspect ratio of the opening diameter of the opening 32A to the height of the intramembrane space 32 (that is, the value obtained by dividing the opening diameter of the opening 32A by the height of the intramembrane space 32) cannot exceed 2. It is noted that in a case where a single-layer porous membrane 30 is used, the membrane thickness is preferably 0.5 to 10 µm. Further, in a case where a plurality of porous membranes 30 are laminated and used, the total membrane thickness of the porous membranes 30 is desirably 10 to 200 μm.

A microfluidic device 110 has a pair of holding plates 38 as holding members that hold the cavity unit 16 in a state of being compressed in the thickness direction. The pair of holding plates 38 are provided separately from the cavity unit 16 at both ends of the cavity unit 16 in the thickness direction, that is, on the upper side of the upper cavity member 12 and on the lower side of the lower cavity member 14, and the sizes thereof are set to respectively cover the entire upper surface of the upper cavity member 12 and the entire lower surface of the lower cavity member 14.

As illustrated in FIG. 2, a plurality (eight in present embodiment) of bolt holes 40 are respectively formed at corresponding positions in the pair of holding plate 38, where bolt holes 40 penetrate the holding plates 38 in the thickness direction. The holding plate 38 provided on the upper side of the upper cavity member 12 has the through-holes 22A, 22B, 28A, and 28B that respectively communicate with the through-holes 42A, 42B, 44A, and 44B of the upper cavity member 12.

As illustrated in FIG. 1, inflow tubes 62A and 64A are respectively connected to the through-holes 42A and 44A, and outflow tubes 62B and 64B are respectively connected to the through-holes 42B and 44B. Various treatment liquids and cell suspensions flow into the upper micro flow channel 18 and the lower micro flow channel 24 through the inflow tubes 62A and 64A. The various treatment liquids and cell suspensions that have passed through the upper micro flow channel 18 and the lower micro flow channel 24 flow out from the outflow tubes 62B and 64B.

A plurality (eight in present embodiment) of the spacers 46 that define spacings between the holding plates 38 are provided outside the recessed part 29 of the cavity unit 16 between the pair of the holding plates 38. The spacers 46 are cylindrical members having an inner diameter substantially the same as an inner diameter of the bolt hole 40 and are disposed at positions corresponding to the bolt holes 40, respectively.

The pair of holding plates 38 are joined to each other by a plurality of bolts 50 that are inserted into the bolt holes 40 and the spacers 46 and fixed by nuts 48. At this time, the upper cavity member 12 and the lower cavity member 14 are compressed and held in a state where the porous membrane 30 are sandwiched therebetween, by the pair of holding plates 38.

Figure 5:
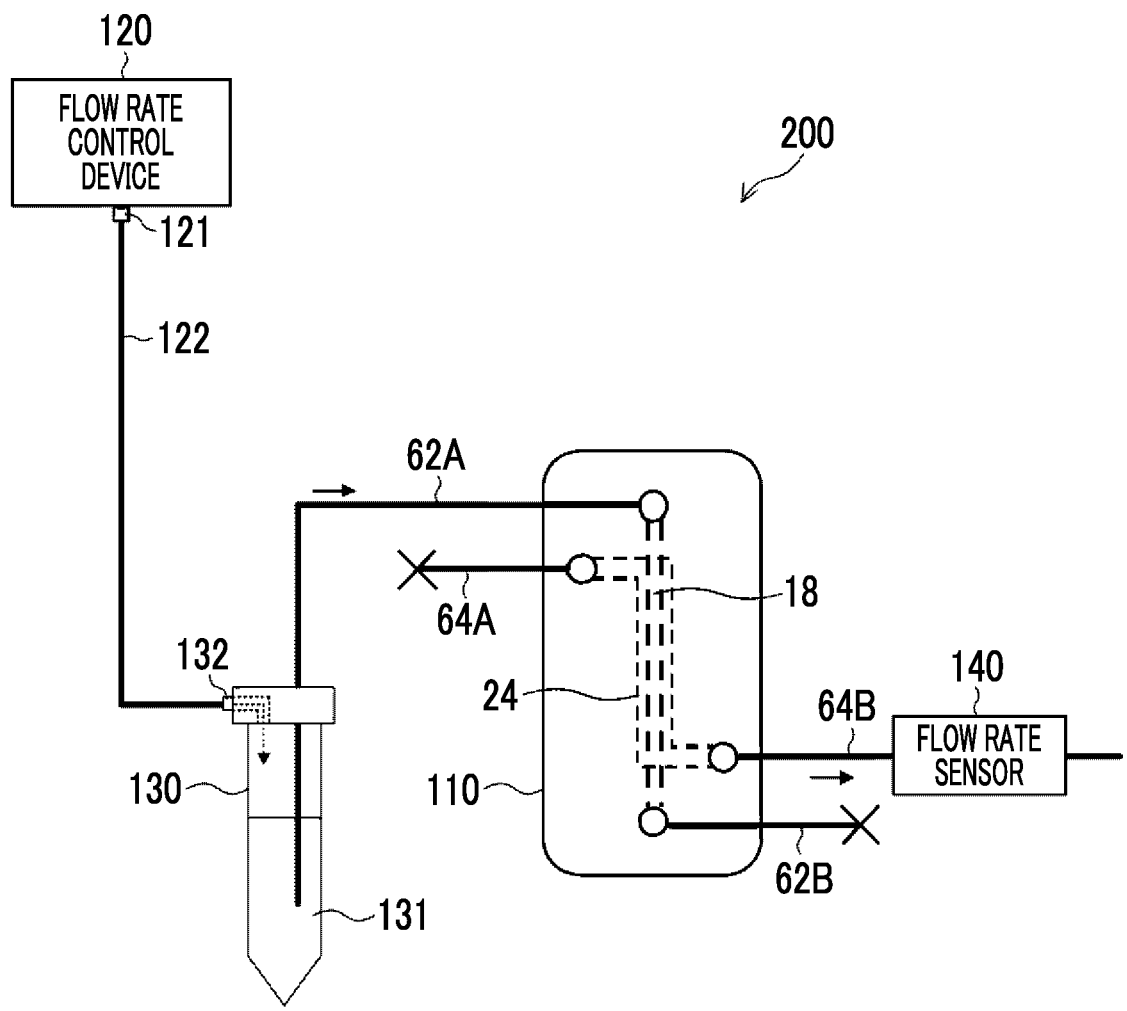
FIG. 5 is a view illustrating an example of an evaluation system according to an embodiment of the present disclosed technology.

FIG. 5 is a view illustrating an example of a configuration of an evaluation system 200 that is used for evaluating the permeability of the porous membrane according to the embodiment of the present disclosed technology. The evaluation system 200 is constituted to include a flow rate control device 120, a storage unit 130, and a flow rate sensor 140 in addition to the microfluidic device 110.

The storage unit 130 stores a liquid 131 that is supplied to the upper micro flow channel 18 of the microfluidic device 110. The tip part of the inflow tube 62A connected to the upper micro flow channel 18 is inserted into the liquid 131 stored in the storage unit 130.

The flow rate control device 120 has a function of controlling the flow rate (the volume per unit time) of the liquid 131 that is supplied to the upper micro flow channel 18 of the microfluidic device 110. One end of an air supply tube 122 is connected to an exhaust port 121 of the flow rate control device 120, and the other end of the air supply tube 122 is connected to a gas introduction port 132 of the storage unit 130. In a case where the gas is discharged from the exhaust port 121 of the flow rate control device 120, the pressure inside the storage unit 130 rises, and thus the liquid 131 stored in the storage unit 130 is supplied to the upper micro flow channel 18. The flow rate control device 120 controls the flow rate of the liquid 131 that is supplied to the upper micro flow channel 18 by controlling the pressure (hereinafter, referred to as the supply pressure) of the gas that is discharged from the exhaust port 121. The supply pressure is a pressure against the liquid surface of the liquid 131 stored in the storage unit 130. The supply pressure can be freely set by a user, and the supply pressure can be continuously changed. As the flow rate control device 120, for example, ELVEFLOW (registered trade name) manufactured by ELVESYS can be used.

The flow rate sensor 140 is connected to the outflow tube 64B connected to the lower micro flow channel 24. The flow rate sensor 140 detects the flow rate of the liquid that flows through the lower micro flow channel 24 and outputs the detected flow rate.

The outflow tube 62B connected to the upper micro flow channel 18 and the inflow tube 64A connected to the lower micro flow channel 24 are each in a closed state.

Figure 6:
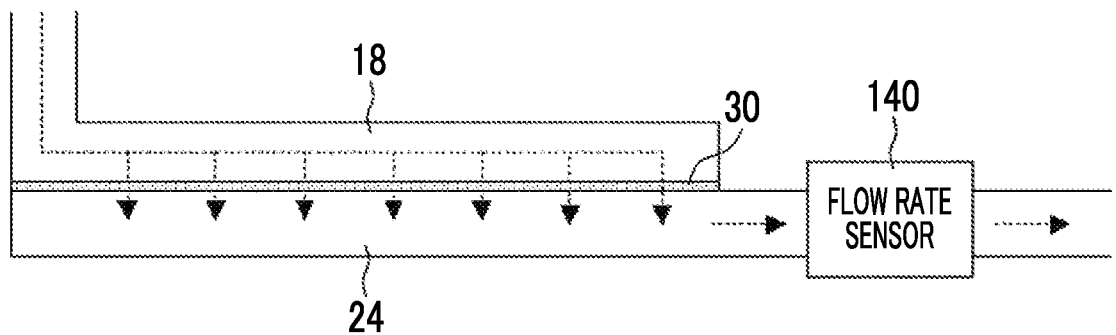
FIG. 6 is a view schematically illustrating a flow channel configuration of the evaluation system according to an embodiment of the present disclosed technology.
Figure 7:
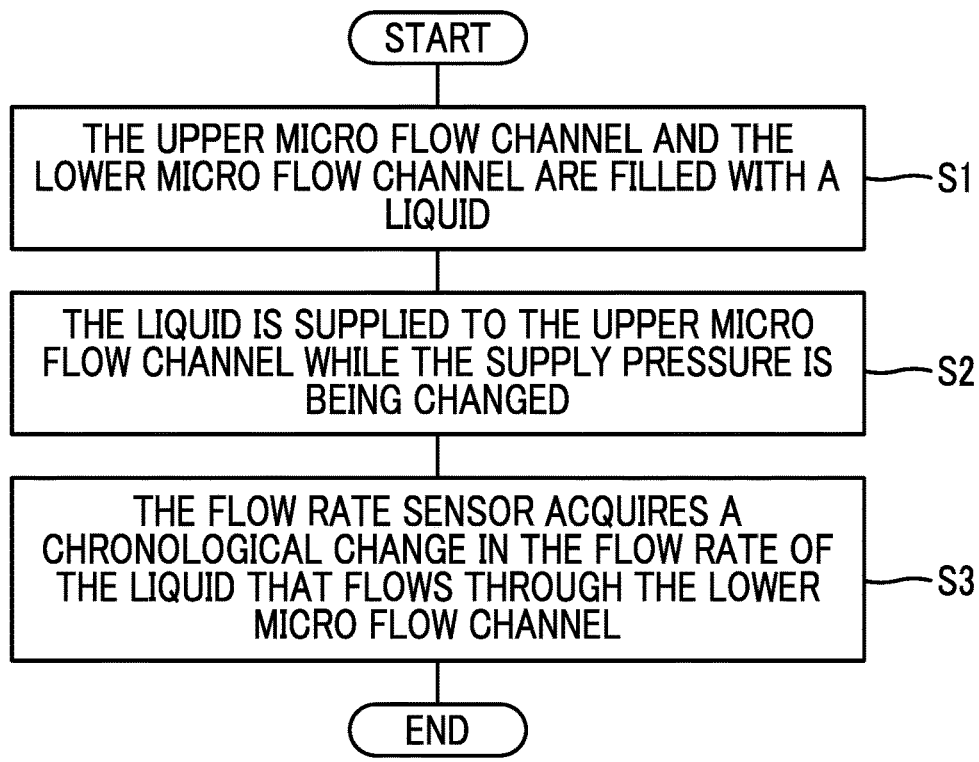
FIG. 7 is a flowchart illustrating an example of an evaluation method for permeability of a porous membrane according to an embodiment of the present disclosed technology.

Hereinafter, an evaluation method for the permeability of the porous membrane 30 according to the embodiment of the present disclosed technology, using the evaluation system 200, will be described. FIG. 6 is a view schematically illustrating a flow channel configuration of the evaluation system 200. FIG. 7 is a flowchart illustrating an example of an evaluation method for permeability of the porous membrane 30 according to an embodiment of the present disclosed technology.

First, the upper micro flow channel 18 and the lower micro flow channel 24 are each filled with a liquid (a step S1). Then, the flow rate control device 120 is operated. The supply pressure of the flow rate control device 120 is set so that it changes chronologically. That is, the liquid 131 is supplied to the upper micro flow channel 18 while the supply pressure is being changed (a step S2). As the supply pressure changes chronologically, the flow rate of the liquid 131 that is supplied from the storage unit 130 to the upper micro flow channel 18 changes. As the liquid 131 is supplied to the upper micro flow channel 18 filled with the liquid in advance, the liquid accommodated in the upper micro flow channel 18 permeates through the porous membrane 30 and flows out to the lower micro flow channel 24. As a result, a liquid flow is generated in the lower micro flow channel 24. The flow rate of the liquid that flows through the lower micro flow channel 24 changes in response to the supply pressure in the flow rate control device 120 and also becomes dependent on the permeability of the porous membrane 30. Next, the flow rate sensor 140 acquires, as an evaluation indicator, a chronological change in the flow rate of the liquid that flows through the lower micro flow channel 24 (a step S3).

Figure 8:
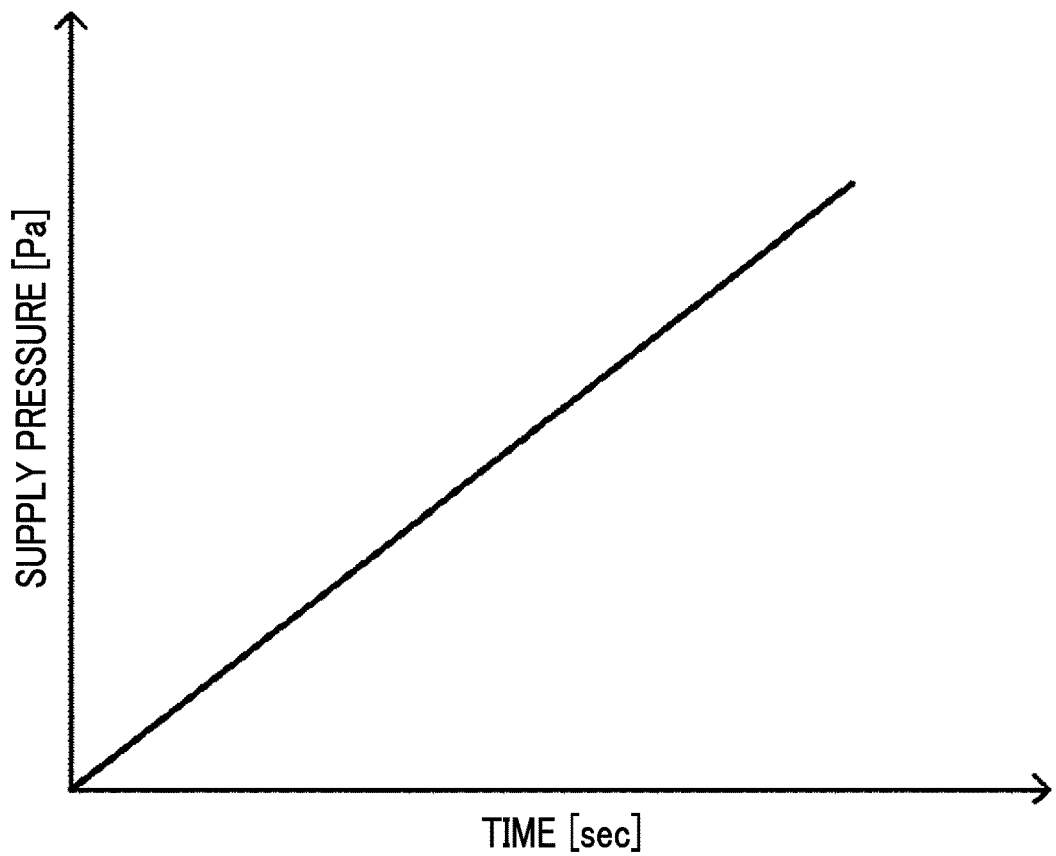
FIG. 8 is a graph illustrating an example of a time course of supply pressure in a flow rate control device according to an embodiment of the present disclosed technology.
Figure 9:
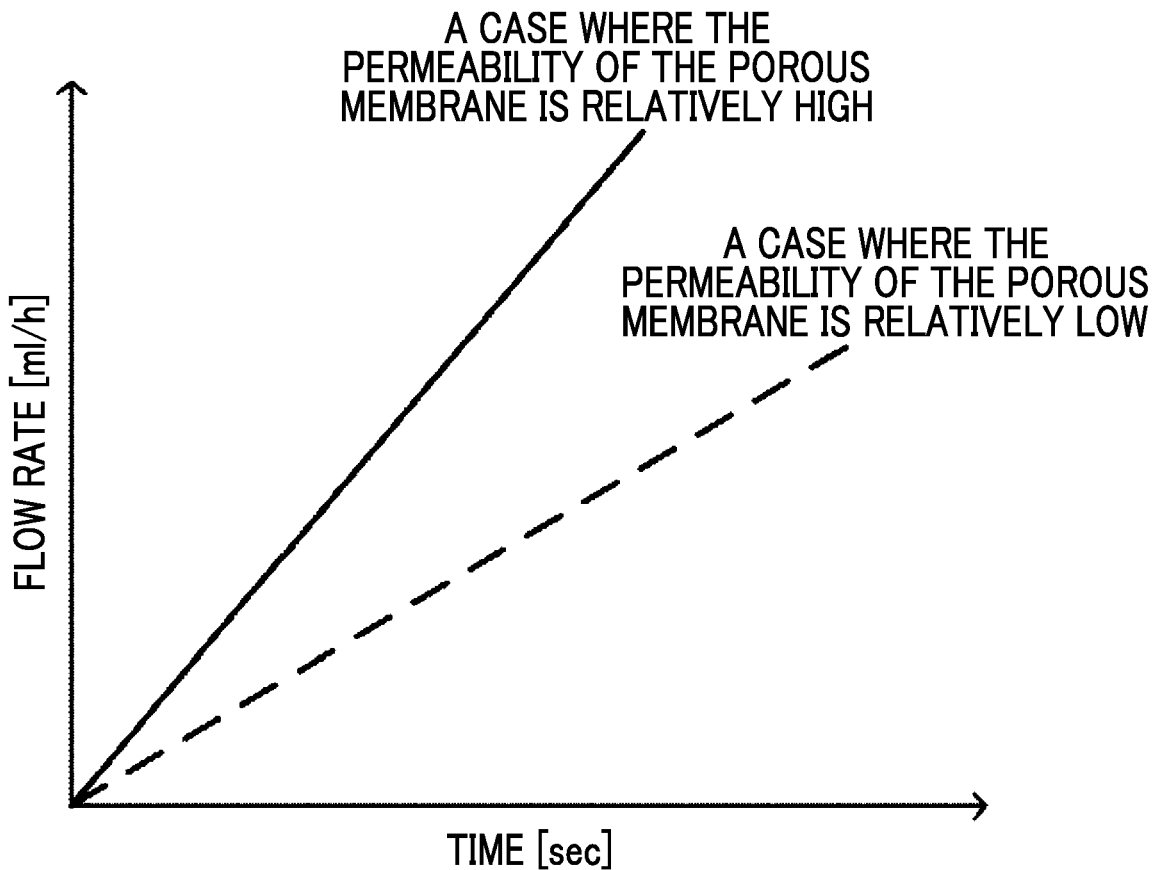
FIG. 9 is a graph illustrating an example of a time course of a flow rate of a liquid that flows through a lower micro flow channel according to an embodiment of the present disclosed technology.

FIG. 8 is a graph illustrating an example of a time course of supply pressure in the flow rate control device 120. As illustrated in FIG. 8, the supply pressure may be set to change linearly in time. FIG. 9 is a graph illustrating an example of a time course of the flow rate of the liquid that flows through the lower micro flow channel 24 in a case where the supply pressure is linearly changed in time. In FIG. 9, the solid line corresponds to a case where the permeability of the porous membrane 30 is relatively high, and the dotted line corresponds to a case where the permeability of the porous membrane 30 is relatively low. In a case where the permeability of the porous membrane 30 is relatively high, the rate of change (the slope) of the flow rate of the liquid that flows through the lower micro flow channel 24 becomes higher than that in a case where the permeability of the porous membrane 30 is relatively low. As a result, it is possible to evaluate the permeability of the porous membrane 30 by monitoring the flow rate of the liquid that flows through the lower micro flow channel 24.

A graph showing the time course of the flow rate, as illustrated in FIG. 9, may be acquired as the chronological change of the flow rate of the liquid that flows through the lower micro flow channel 24, which is acquired in the step S3. In addition, a rate of change (the slope) of the flow rate of the liquid that flows through the lower micro flow channel 24 may be acquired as the chronological change of the flow rate of the liquid that flows through the lower micro flow channel 24. Specifically, in a case where the amount of change in the flow rate of the liquid that flows through the lower micro flow channel 24 in the period $\Delta T$ is denoted by $\Delta Q$, $\Delta Q/\Delta t$ may be acquired as the above rate of change (the slope). Further, in a case where the flow rate of the liquid that flows through the lower micro flow channel 24 is denoted by $Q_1$ in a case where the supply pressure is $P_1$, $Q_1/P_1$ may be acquired as a chronological change in the flow rate of the liquid that flows through the lower micro flow channel 24. In addition, in a case where the flow rates of the liquids that flow through the lower micro flow channel 24 at different supply pressures $P_1, P_2, \ldots, P_n$ are respectively denoted by $Q_1, Q_2, \ldots, Q_n$, the average value of $Q_1/P_1$, $Q_2/P_2, \ldots, Q_n/P_n$ may be acquired as a chronological change of the flow rate of the liquid that flows through the lower micro flow channel 24.

Figure 10:
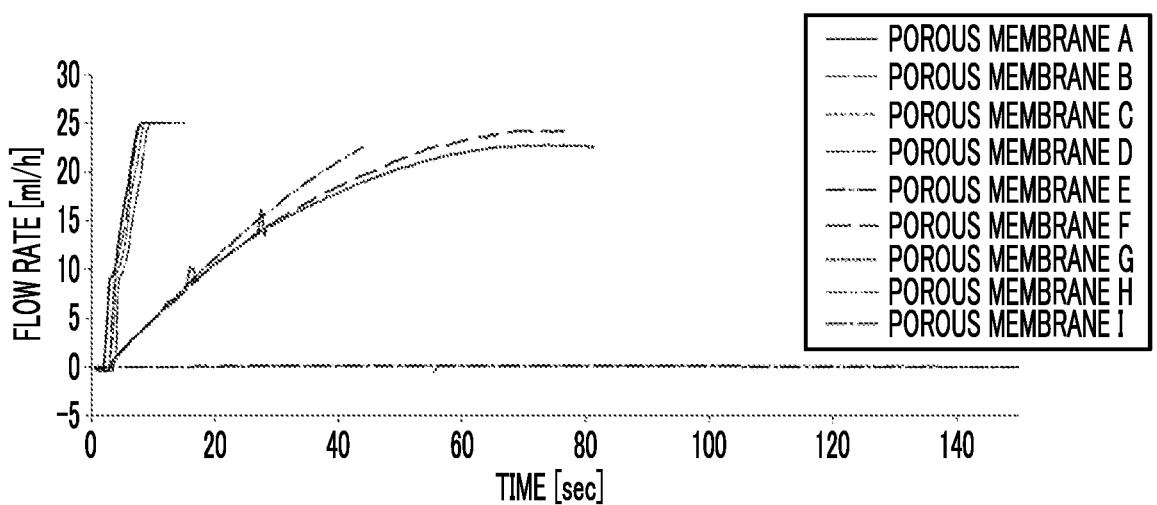
FIG. 10 is a graph showing an example of results of evaluating the permeability of a plurality of kinds of porous membranes having different pore diameters or opening ratios by using the evaluation method according to the embodiment of the present disclosed technology.

FIG. 10 is a graph showing an example of results of evaluating the permeability of a plurality of kinds of porous membranes having different pore diameters or opening ratios by using the evaluation method according to the embodiment of the present disclosed technology. That is, FIG. 10 a graph showing, regarding each of the plurality of kinds of porous membranes A to I, the time course of the flow rate of the liquid that flows through the lower micro flow channel 24 in a case where the supply pressure is linearly changed in time. The outlines of the porous membranes A to I are summarized in Table 1 below.

TABLE 1

|  | Kind | Pore diameter | Opening ratio |
| --- | --- | --- | --- |
| Porous membrane A | Millipore 3 μm | 3 μm | 14.1% |
| Porous membrane B | Millipore 5 μm | 5 μm | 11.8% |
| Porous membrane C | Millipore 5 μm | 5 μm | 11.8% |
| Porous membrane D | Millipore 3 μm | 3 μm | 14.1% |
| Porous membrane E | Millipore 0.4 μm | 0.4 μm | 12.6% |
| Porous membrane F | Falcon 0.4 (HD) | 0.4 μm | 12.6% |
| Porous membrane G | Falcon 0.4 (HD) | 0.4 μm | 12.6% |
| Porous membrane H | Falcon 0.4 (LD) | 0.4 μm | 0.2% |
| Porous membrane I | Falcon 0.4 (LD) | 0.4 μm | 0.2% |

FIG. 10 shows results that the larger the pore diameter of the porous membrane and the larger the opening ratio of the porous membrane, the larger the rate of change (the slope) of the flow rate of the liquid that flows through the lower micro flow channel 24. It is noted that in the porous membrane F and the porous membrane the change in the flow rate with respect to the time change is non-linear since an unintended leak has occurred in the flow channel.

As described above, in the evaluation method for permeability of a porous membrane according to the embodiment of the present disclosed technology, the change that occurs in the liquid accommodated in the lower micro flow channel 24 is acquired as an evaluation indicator of the permeability of the porous membrane in a case where the liquid is supplied to the upper micro flow channel 18 while the supply pressure is being changed. In the present embodiment, a chronological change in the flow rate of the liquid that flows through the lower micro flow channel 24 is acquired as "the change that occurs in the liquid accommodated in the lower micro flow channel 24".

According to the evaluation method according to the embodiment of the present disclosed technology, it is possible to evaluate the permeability of the porous membrane in a short time as compared with, for example, a method of monitoring an amount of light radiated from a phosphor that leaks into the second flow channel, where a liquid containing a phosphor is accommodated in the upper micro flow channel 18, a liquid containing no phosphor is accommodated in the lower micro flow channel 24, and the phosphor diffuses in a liquid and permeates through a porous membrane to leak to the lower micro flow channel 24.

Second Embodiment

Figure 11:
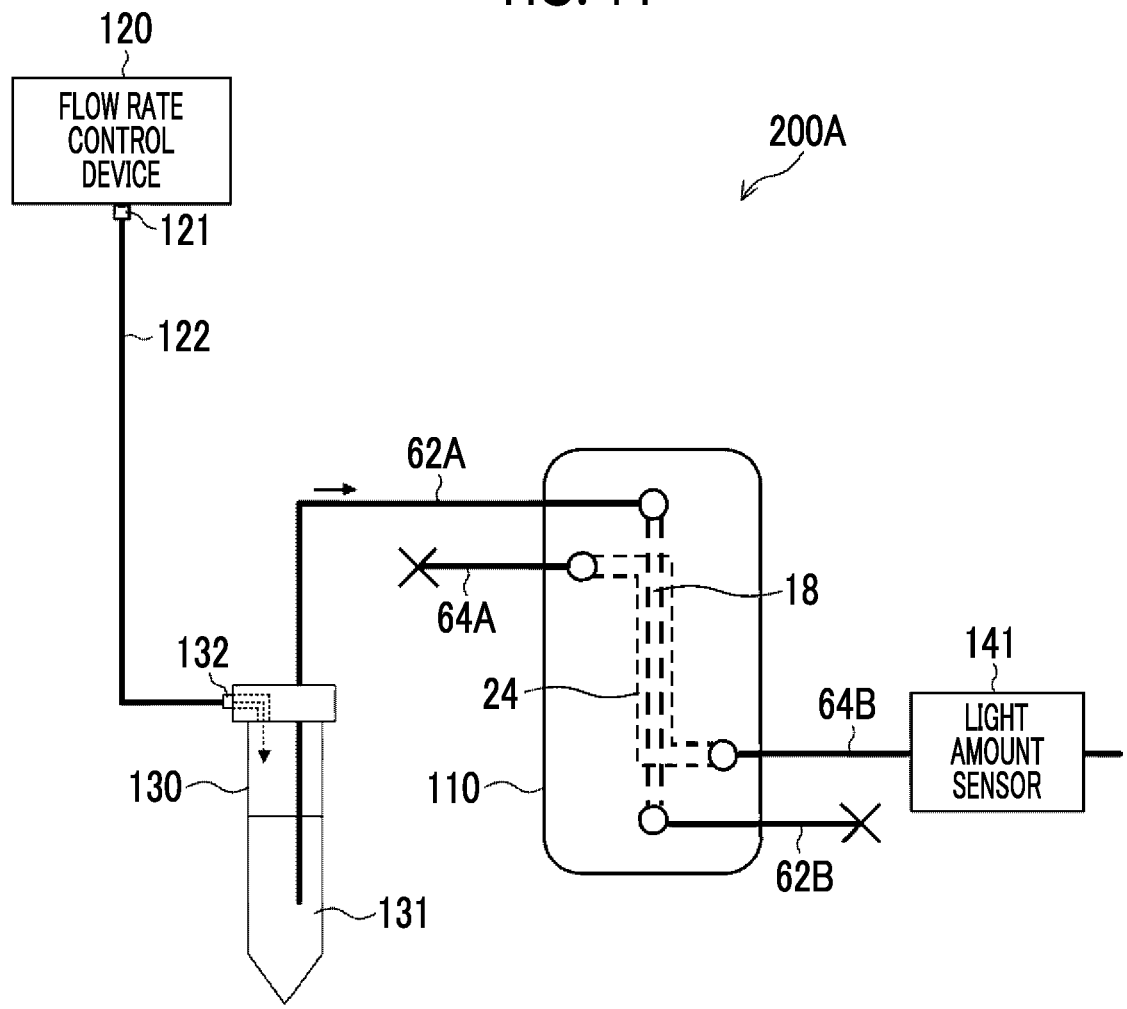
FIG. 11 is a view illustrating an example of an evaluation system according to another embodiment of the present disclosed technology.
Figure 12:
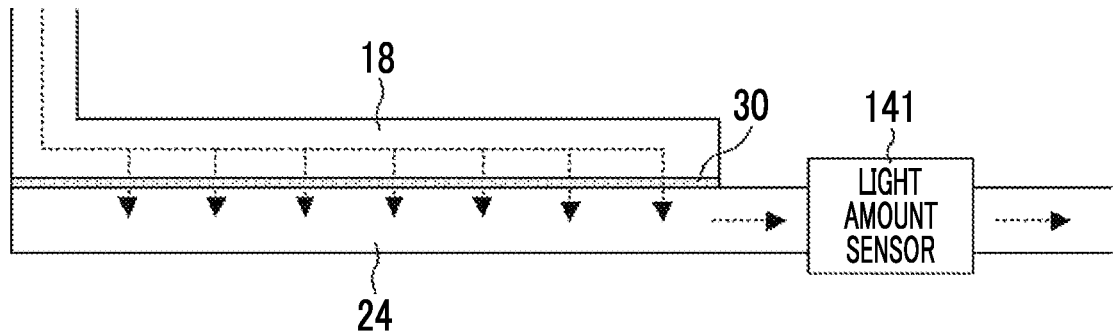
FIG. 12 is a view schematically illustrating a flow channel configuration of the evaluation system according to another embodiment of the present disclosed technology.

FIG. 11 is a view illustrating an example of an evaluation system 200A according to the second embodiment of the present disclosed technology. FIG. 12 is a view schematically illustrating a flow channel configuration of the evaluation system 200A. The evaluation system 200A includes a light amount sensor 141 instead of the flow rate sensor 140 in the evaluation system 200 according to the first embodiment.

Hereinafter, an evaluation method for the permeability of the porous membrane 30 according to the second embodiment of the present disclosed technology, using the evaluation system 200A, will be described. FIG. 13 is a flowchart illustrating an example of an evaluation method for permeability of the porous membrane 30 according to the second embodiment of the present disclosed technology.

First, the upper micro flow channel 18 is filled with a liquid containing a phosphor (a step S11). Next, the lower micro flow channel 24 is filled with a liquid containing no phosphor (a step S12). Then, the flow rate control device 120 is operated. The supply pressure of the flow rate control device 120 is set so that it changes chronologically. The liquid 131 containing a phosphor is accommodated in the storage unit 130. That is, the liquid 131 that contains a phosphor is supplied to the upper micro flow channel 18 while the supply pressure is being changed (a step S13). As the supply pressure changes, the flow rate of the liquid 131 that is supplied from the storage unit 130 to the upper micro flow channel 18 changes. As the liquid 131 that contains a phosphor is supplied to the upper micro flow channel 18 filled with the liquid that contains a phosphor in advance, the liquid that contains a phosphor, which is accommodated in the upper micro flow channel 18, permeates through the porous membrane 30 and flows out to the lower micro flow channel 24. As a result, a liquid flow due to the liquid that contains a phosphor is generated in the lower micro flow channel 24. The liquid that flows through the lower micro flow channel 24 is irradiated with excitation light from a light source, which is not illustrated in the drawing. As a result, light is radiated from the phosphor contained in the liquid that flows through the lower micro flow channel 24. The rate of change in the amount of light (hereinafter, referred to as the fluorescent light amount) radiated from the phosphor contained in the liquid that flows through the lower micro flow channel 24 changes in response to the supply pressure in the flow rate control device 120 and also becomes dependent on the permeability of the porous membrane 30. Next, the light amount sensor 141 acquires the chronological change of the fluorescent light amount as an evaluation indicator (a step S14).

FIG. 14 is a graph illustrating an example of a time course of a fluorescent light amount in a case where the supply pressure is linearly changed in time. In FIG. 14, the solid line corresponds to a case where the permeability of the porous membrane 30 is relatively high, and the dotted line corresponds to a case where the permeability of the porous membrane 30 is relatively low. In a case where the permeability of the porous membrane 30 is relatively high, the rate of change (the slope) of the fluorescent light amount becomes higher than that in a case where the permeability of the porous membrane 30 is relatively low. As a result, it is possible to evaluate the permeability of the porous membrane 30 by monitoring the fluorescent light amount.

A graph showing the time course of the fluorescent light amount, as illustrated in FIG. 14, may be acquired as the chronological change of the fluorescent light amount, which is acquired in the step S14. In addition, the rate of change (the slope) of the fluorescent light amount may be acquired as the chronological change of the fluorescent light amount. Specifically, in a case where the amount of change of the fluorescent light amount in the period $\Delta T$ is denoted by $\Delta L$, $\Delta L/\Delta t$ may be acquired as the above rate of change (the slope). In addition, in a case where the fluorescent light amount is denoted by $L_1$ in a case where the supply pressure is denoted by $P_1$, $L_1/P_1$ may be acquired as a chronological change of the fluorescent light amount. In a case where the fluorescent light amounts at different supply pressures $P_1$, $P_2$, ..., $P_n$ are respectively denoted by $L_1$, $L_2$, ..., $L_n$, the average value of $L_1/P_1$, $L_2/P_2$, ..., $L_n/P_n$ may be acquired as a chronological change in the fluorescent light amount.

As described above, in the present embodiment, a chronological change in the amount of light radiated from the phosphor contained in the liquid that flows through the lower micro flow channel 24 is acquired as "the change that occurs in the liquid accommodated in the lower micro flow channel 24". According to the evaluation method according to the present embodiment, it is possible to evaluate the permeability of the porous membrane in a short time as in the evaluation method according to the first embodiment.

Third Embodiment

Figure 15:
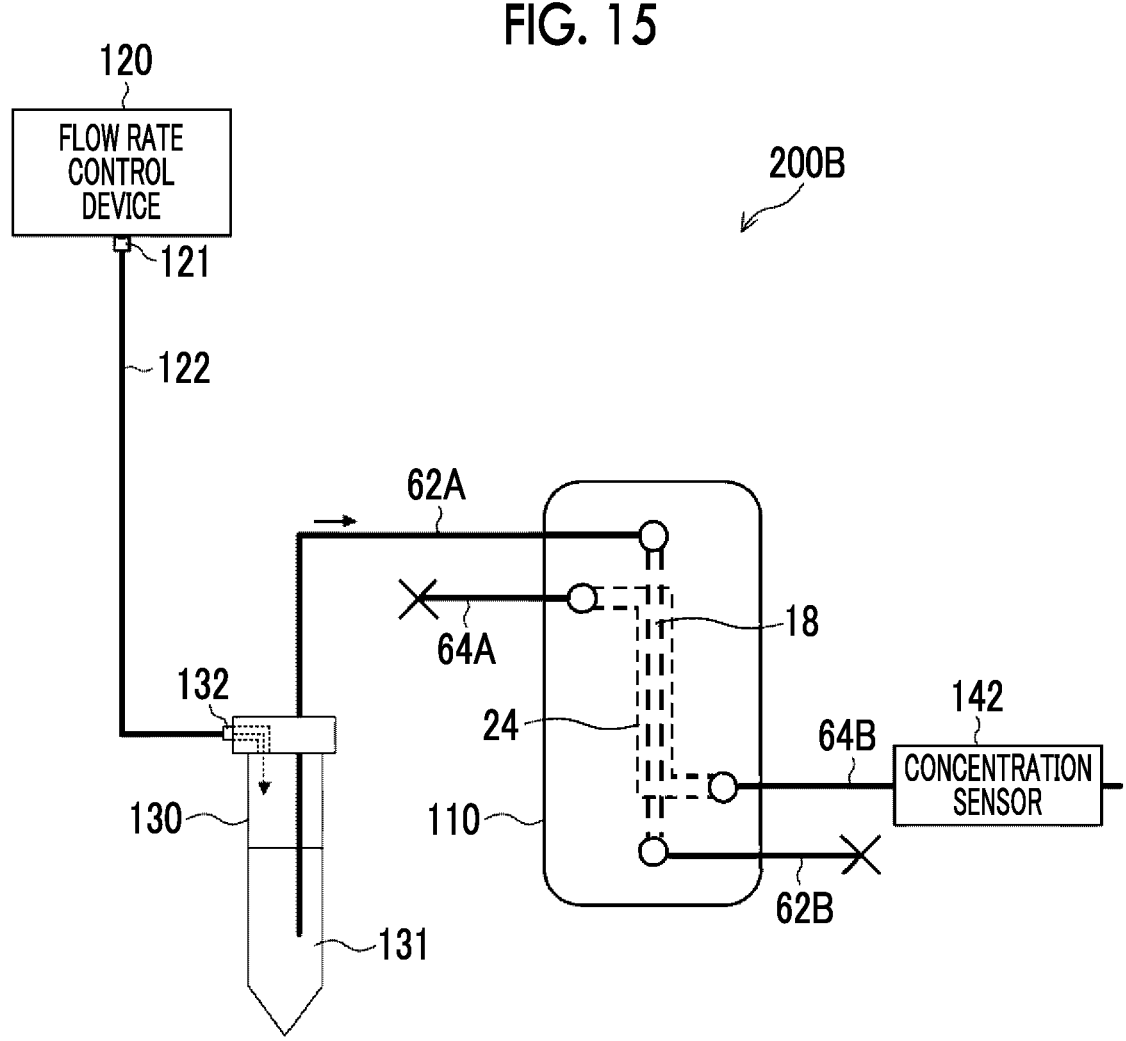
FIG. 15 is a view illustrating an example of an evaluation system according to another embodiment of the present disclosed technology.
Figure 16:
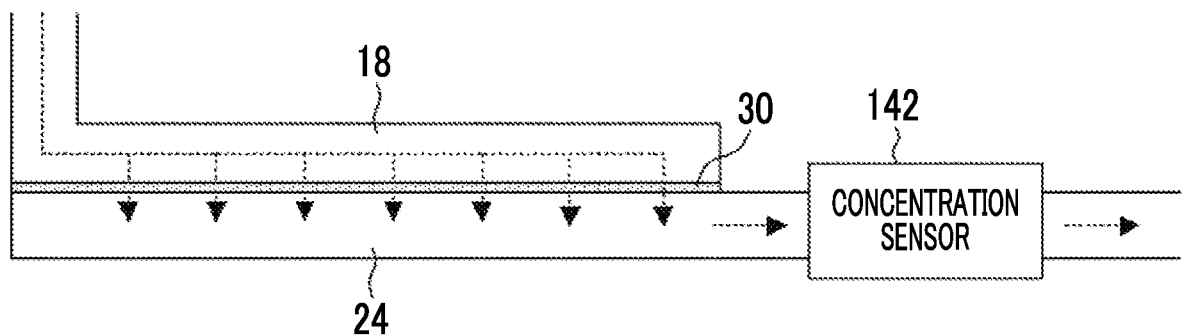
FIG. 16 is a view schematically illustrating a flow channel configuration of the evaluation system according to another embodiment of the present disclosed technology.

FIG. 15 is a view illustrating an example of an evaluation system 200B according to the third embodiment of the present disclosed technology. FIG. 16 is a view schematically illustrating a flow channel configuration of the evaluation system 200B. The evaluation system 200B includes a concentration sensor 142 instead of the flow rate sensor 140 in the evaluation system 200 according to the first embodiment.

Hereinafter, an evaluation method for the permeability of the porous membrane 30 according to the third embodiment of the present disclosed technology, using the evaluation system 200B, will be described. FIG. 17 is a flowchart illustrating an example of an evaluation method for permeability of the porous membrane 30 according to the third embodiment of the present disclosed technology.

First, the upper micro flow channel 18 is filled with a liquid containing a specific component (a step S21). Next, the lower micro flow channel 24 is filled with a liquid containing no specific component (a step S22). Then, the flow rate control device 120 is operated. The supply pressure of the flow rate control device 120 is set so that it changes chronologically. The liquid 131 containing a specific component is accommodated in the storage unit 130. That is, the liquid 131 that contains a specific component is supplied to the upper micro flow channel 18 while the supply pressure is being changed (a step S23). As the supply pressure changes, the flow rate of the liquid 131 that is supplied from the storage unit 130 to the upper micro flow channel 18 changes. As the liquid 131 that contains a specific component is supplied to the upper micro flow channel 18 filled with the liquid that contains a specific component in advance, the liquid that contains a specific component, which is accommodated in the upper micro flow channel 18, permeates through the porous membrane 30 and flows out to the lower micro flow channel 24. As a result, a liquid flow due to the liquid that contains a specific component is generated in the lower micro flow channel 24. The rate of change in the concentration of the specific component in the liquid that flows through the lower micro flow channel 24 (hereinafter, referred to as the specific component concentration) changes in response to the supply pressure in the flow rate control device 120 and also becomes dependent on the permeability of the porous membrane 30. Next, the concentration sensor 142 acquires the chronological change of the specific component concentration as an evaluation indicator (a step S24). It is noted that the specific component may be any substance that can be quantified, and examples thereof include a dye, a conductive substance, an enzyme, a nanoparticle, a substance containing a radioisotope, a nucleic acid, and a sugar chain. Most substances can be quantified by using techniques such as liquid chromatography.

FIG. 18 is a graph illustrating an example of a time course of a specific component concentration in a case where the supply pressure is linearly changed in time. In FIG. 18, the solid line corresponds to a case where the permeability of the porous membrane 30 is relatively high, and the dotted line corresponds to a case where the permeability of the porous membrane 30 is relatively low. In a case where the permeability of the porous membrane 30 is relatively high, the rate of change (the slope) of the specific component concentration becomes higher than that in a case where the permeability of the porous membrane 30 is relatively low. As a result, it is possible to evaluate the permeability of the porous membrane 30 by monitoring the specific component concentration.

A graph showing the time course of the specific component concentration, as illustrated in FIG. 18, may be acquired as the chronological change of the specific component concentration, which is acquired in the step S24. In addition, the rate of change (the slope) of the specific component concentration may be acquired as the chronological change of the specific component concentration. Specifically, in a case where the amount of change of the specific component concentration in the period $\Delta T$ is denoted by $\Delta C$, $\Delta C/\Delta t$ may be acquired as the above rate of change (the slope). In addition, in a case where the specific component concentration is denoted by $C_1$ in a case where the supply pressure is denoted by $P_1$, $C_1/P_1$ may be acquired as a chronological change of the specific component concentration. In a case where the specific component concentration at different supply pressures $P_1$, $P_2$, ..., $P_n$ are respectively denoted by $C_1$, $C_2$, ..., $C_n$, the average value of $C_1/P_1$, $C_2/P_2$, ..., $C_n/P_n$ may be acquired as a chronological change in the specific component concentration.

According to the evaluation method according to the present embodiment, it is possible to evaluate the permeability of the porous membrane in a short time as in the evaluation method according to the first embodiment.

Fourth Embodiment

Figure 19:
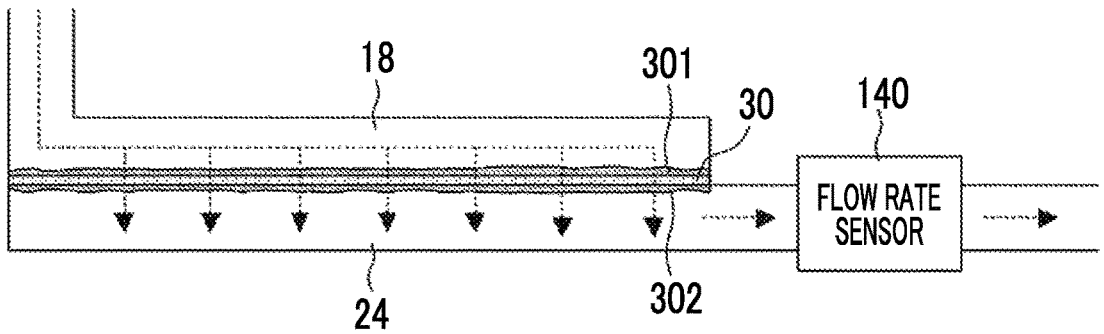
FIG. 19 is a flow channel configuration view illustrating an example of a cell evaluation method according to another embodiment of the present disclosed technology.
Figure 20:
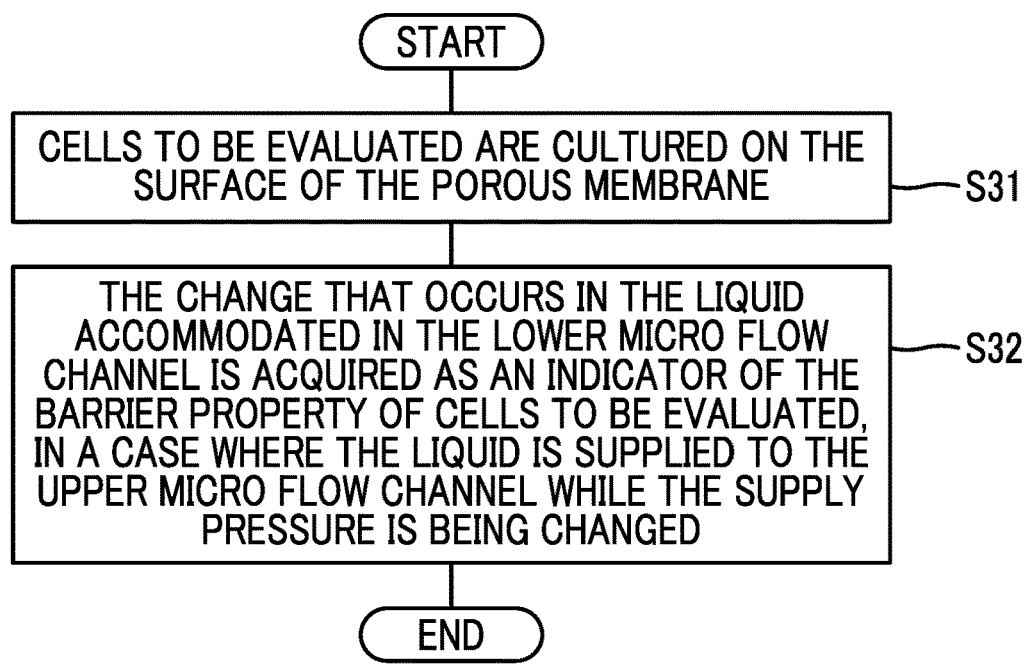
FIG. 20 is a flowchart illustrating an example of a cell evaluation method according to another embodiment of the present disclosed technology.

FIG. 19 and FIG. 20 are respectively a flow channel configuration view and a flowchart, illustrating an example of a cell evaluation method according to the fourth embodiment of the present disclosed technology.

The cell evaluation method according to the present embodiment includes culturing cells to be evaluated on the surface of the porous membrane 30 of the microfluidic device 110 (a step S31). For example, endothelial cells 301 may be cultured on the surface of the porous membrane 30 on the side of the upper micro flow channel 18, and smooth muscle cells 302 may be cultured on the surface of the porous membrane 30 on the side of the lower micro flow channel 24. This makes it possible to form a structure that simulates the blood vessel (the artery) in the microfluidic device 110. The endothelial cells 301 and the smooth muscle cells 302 are cultured in a state of being immersed in the culture solution accommodated in the upper micro flow channel 18 and the lower micro flow channel 24, respectively. It is noted that the cells to be evaluated may be cultured only on one surface of the porous membrane 30.

The cell evaluation method according to the present embodiment includes acquiring the evaluation indicator of the permeability of the porous membrane 30 according to any one of the first to third embodiments described above, as an indicator of the barrier property of cells to be evaluated, which are cell cultured on the surface of the porous membrane 30. That is, the change that occurs in the liquid accommodated in the lower micro flow channel 24 is acquired as an indicator of the barrier property of cells to be evaluated, in a case where the liquid is supplied to the upper micro flow channel 18 while the supply pressure is being changed (a step S32). Here, the barrier property of cells means the performance of cells to be evaluated, which are cultured on the surface of the porous membrane 30, where the performance is the blocking of leakage of the liquid that is supplied to the upper micro flow channel 18 to the lower micro flow channel 24.

In a case where cells cultured on the surface of the porous membrane 30 are healthy, the barrier property of cells suppresses the outflow of the liquid from the upper micro flow channel 18 to the lower micro flow channel 24. On the other hand, in a case where an abnormality occurs in cells cultured on the surface of the porous membrane 30 and the barrier property of cells decreases, the outflow amount of the liquid from the upper micro flow channel 18 to the lower micro flow channel 24 increases. As a result, it is possible to use the evaluation indicator of the permeability of the porous membrane 30 according to the first to third embodiments described above, as an indicator of the barrier property of cells to be evaluated, which are cells cultured on the surface of the porous membrane 30.

For example, in a case where the evaluation indicator of the permeability of the porous membrane 30 according to the first embodiment is used as an indicator of the barrier property of cells to be evaluated, the chronological change of the flow rate of the liquid that flows through the lower micro flow channel is used as an indicator of the barrier property of cells to be evaluated, in a case where the liquid is supplied to the upper micro flow channel 18 while the supply pressure is being changed.

According to the cell evaluation method according to the present embodiment, it is possible to evaluate the barrier property of cells in a short time as compared with, for example, a method of monitoring an amount of light radiated from a phosphor that leaks into the second flow channel, where a liquid containing a phosphor is accommodated in the upper micro flow channel 18, a liquid containing no phosphor is accommodated in the lower micro flow channel 24, and the phosphor diffuses in a liquid and permeates through a porous membrane to leak to the lower micro flow channel 24.

Fifth Embodiment

Figure 21:
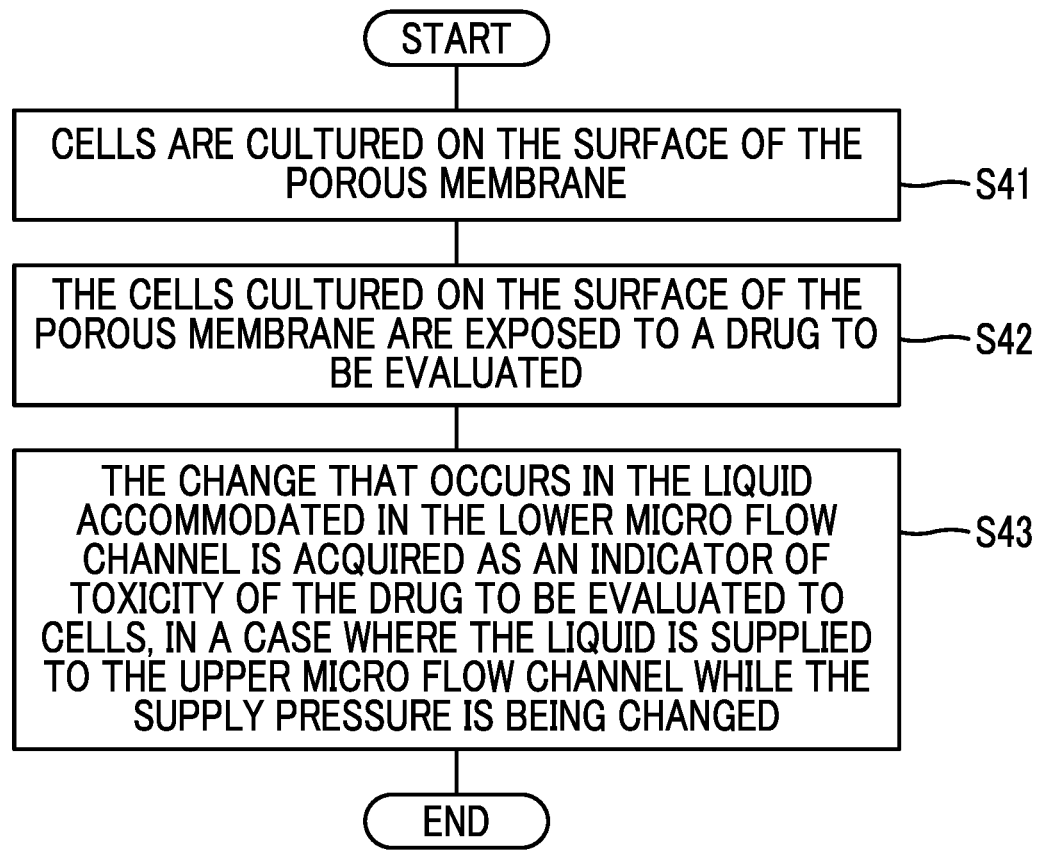
FIG. 21 is a flowchart illustrating an example of a drug evaluation method according to another embodiment of the present disclosed technology.

FIG. 21 is a flowchart illustrating an example of a drug evaluation method according to the fifth embodiment of the present disclosed technology.

The drug evaluation method according to the present embodiment includes culturing cells on the surface of the porous membrane 30 of the microfluidic device 110 (a step S41). For example, as illustrated in FIG. 19, the endothelial cells 301 may be cultured on the surface of the porous membrane 30 on the side of the upper micro flow channel 18, and the smooth muscle cells 302 may be cultured on the surface of the porous membrane 30 on the side of the lower micro flow channel 24. This makes it possible to form a structure that simulates the blood vessel (the artery) in the microfluidic device 110. It is noted that the cells to be evaluated may be cultured only on one surface of the porous membrane 30.

The drug evaluation method according to the present embodiment includes exposing cells cultured on the surface of the porous membrane 30 to a drug to be evaluated (a step S42). That is, a liquid containing a drug to be evaluated is supplied to each of the upper micro flow channel 18 and the lower micro flow channel 24.

The drug evaluation method according to the present embodiment includes acquiring the evaluation indicator of the permeability of the porous membrane 30 according to any one of the first to third embodiments described above as an indicator of toxicity of the drug to be evaluated to the cells. That is, the change that occurs in the liquid accommodated in the lower micro flow channel 24 is acquired as an indicator of toxicity of the drug to be evaluated to the cells, in a case where the liquid is supplied to the upper micro flow channel 18 while the supply pressure is being changed (a step S43).

In a case where cells cultured on the surface of the porous membrane 30 are healthy, the barrier property of these cells suppresses the outflow of the liquid from the upper micro flow channel 18 to the lower micro flow channel 24. In a case where the drug to be evaluated has toxicity to cells cultured on the surface of the porous membrane 30 and thus the barrier property of the cells decreases, the outflow amount of the liquid from the upper micro flow channel 18 to the lower micro flow channel 24 increases in a case where an abnormality occurs in the cells. As a result, it is possible to use the evaluation indicator of the permeability of the porous membrane 30 according to the first to third embodiments described above, as an indicator of toxicity of the drug to be evaluated to the cells.

For example, in a case where the evaluation indicator of the permeability of the porous membrane 30 according to the first embodiment is acquired as an indicator of the toxicity of the drug to to be evaluated to the cells, the chronological change of the flow rate of the liquid that flows through the lower micro flow channel is acquired as an indicator of toxicity of the drug to be evaluated to the cells, in a case where the liquid is supplied to the upper micro flow channel 18 while the supply pressure is being changed.

Figure 22:
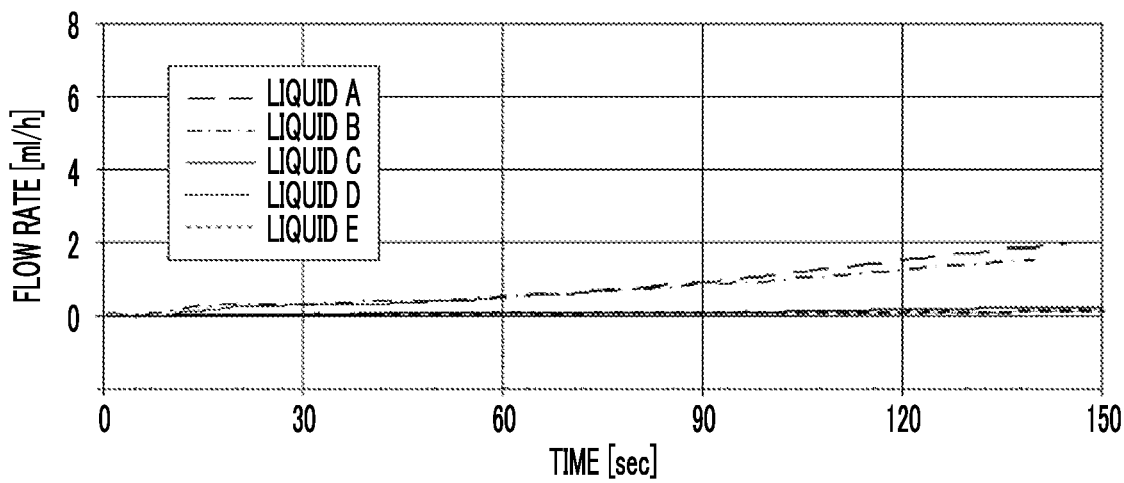
FIG. 22 is a graph showing an example of results of evaluating the toxicity of drugs by using the evaluation method according to the embodiment of the present disclosed technology.

FIG. 22 is a graph showing an example of results of evaluating the toxicity of drugs by using the evaluation method according to the present embodiment. That is, FIG. 22 a graph showing, regarding each of the liquids to be evaluated A to E, the time course of the flow rate of the liquid that flows through the lower micro flow channel 24 in a case where the supply pressure is linearly changed in time. The outlines of the liquids A to E are summarized in Table 2 below. The liquid A and the liquid B are media obtained by adding dimethyl sulfoxide (DMSO) to a basal medium as a solvent, where the media contains cytochalasin having a concentration of 50 μg/ml, which is a drug to be evaluated. The liquid C and the liquid D are media obtained by adding DMSO to a basal medium as a solvent, and they do not contain a drug to be evaluated. The liquid E contains a basal medium and does not contain DMSO and a drug to be evaluated. It is noted that the endothelial cells 301 were cultured on the surface of the porous membrane 30 on the side of the upper micro flow channel 18, and the smooth muscle cells 302 were cultured on the surface of the porous membrane 30 on the side of the lower micro flow channel 24. As the porous membrane 30, Millipore 0.4 μm (pore diameter: 0.4 μm) was used.

TABLE 2

| | Classification | cytochalasin | DMSO |
|---|---|---|---|
| Liquid A | Containing a drug | 50 μg/ml | 0.50% |
| Liquid B | Containing a drug | 50 μg/ml | 0.50% |
| Liquid C | vehicle | — | 0.50% |
| Liquid D | vehicle | — | 0.50% |
| Liquid E | control | — | — |

In a case where cells were exposed to the liquid A and the liquid B, containing cytochalasin as a drug, the rate of change (the slope) of the flow rate of the liquid that flows through the lower micro flow channel 24 was significantly larger than those of Vehicle (the liquid C and the liquid D) and Control (the liquid E). This indicates that the cytochalasin contained in the liquid A and the liquid B has toxicity to the endothelial cells 301 and the smooth muscle cells 302.

According to the drug evaluation method according to the present embodiment, it is possible to evaluate the toxicity of a drug to cells in a short time as compared with, for example, a method of monitoring an amount of light radiated from a phosphor that leaks into the second flow channel, where a liquid containing a phosphor is accommodated in the upper micro flow channel 18, a liquid containing no phosphor is accommodated in the lower micro flow channel 24, and the phosphor diffuses in a liquid and permeates through a porous membrane to leak to the lower micro flow channel 24.

The disclosure of JP2019-169806 filed on Sep. 18, 2019, is incorporated in the present specification in its entirety by reference. In addition, all documents, patent applications, and technical standards described in the present specification are incorporated in the present specification by reference, to the same extent as in the case where each of the documents, patent applications, and technical standards is specifically and individually described.

What is claimed is:

1. An evaluation method for permeability of a porous membrane that is inserted between a first flow channel and a second flow channel, the evaluation method comprising:
acquiring a change that occurs inside a liquid accommodated in the second flow channel as an evaluation indicator of permeability of the porous membrane in a case of supplying a liquid to the first flow channel while changing a supply pressure.

2. An evaluation method for permeability of a porous membrane that separates a first flow channel and a second flow channel, the evaluation method comprising:
supplying a pressure to a liquid inside the first flow channel and acquiring a change that occurs in a liquid accommodated in the second flow channel as an evaluation indicator of permeability of the porous membrane,
wherein a phosphor is contained in the liquid that is supplied to the first flow channel, and
a chronological change in an amount of light radiated from the phosphor contained in the liquid that flows through the second flow channel is acquired as the evaluation indicator.

3. An evaluation method for permeability of a porous membrane that separates a first flow channel and a second flow channel, the evaluation method comprising:
supplying a pressure to a liquid inside the first flow channel and acquiring a change that occurs in a liquid accommodated in the second flow channel as an evaluation indicator of permeability of the porous membrane,
wherein a specific component is contained in the liquid that is supplied to the first flow channel, and
a chronological change in a concentration of the specific component contained in the liquid that flows through the second flow channel is acquired as the evaluation indicator.

4. A cell evaluation method using the evaluation method for permeability of a porous membrane that separates a first flow channel and a second flow channel, the cell evaluation method comprising:
supplying a pressure to a liquid inside the first flow channel and acquiring a change that occurs in a liquid accommodated in the second flow channel as an evaluation indicator of permeability of the porous membrane, and
acquiring the evaluation indicator acquired in a state where cells to be evaluated are cultured on a surface of the porous membrane as an indicator of performance of the cells to be evaluated, the performance being blocking of leakage of a liquid that is supplied to the first flow channel to the second flow channel.

5. A drug evaluation method using an evaluation method for permeability of a porous membrane that separates a first flow channel and a second flow channel, the drug evaluation method comprising:
supplying a pressure to a liquid inside the first flow channel and acquiring a change that occurs in a liquid accommodated in the second flow channel as an evaluation indicator of permeability of the porous membrane, and
culturing cells on a surface of the porous membrane; and acquiring the evaluation indicator acquired after exposing the cells to a drug to be evaluated as an indicator of toxicity of the drug to be evaluated to the cells.

6. An evaluation method for permeability of a porous membrane that separates a first flow channel and a second flow channel, the evaluation method comprising:
supplying a pressure to a liquid inside the first flow channel and acquiring a change that occurs in a liquid accommodated in the second flow channel as an evaluation indicator of permeability of the porous membrane, wherein a microfluidic device having the first flow channel and the second flow channel is used.

\* \* \* \* \*